US012746352B2

(12) United States Patent
Pekoz

(10) Patent No.: US 12,746,352 B2
(45) Date of Patent: Sep. 29, 2026

(54) INTRANASAL TREATMENT DEVICE

(71) Applicant: ISTANBUL UNIVERSITESI REKTORLUGU, Istanbul (TR)

(72) Inventor: Ayca Yildiz Pekoz, Beyazit Fatih (TR)

(73) Assignee: ISTANBUL UNIVERSITESI REKTORLUGU, Istanbul (TR)

( * ) Notice: Subject to any disclaimer, the term of this patent is extended or adjusted under 35 U.S.C. 154(b) by 736 days.

(21) Appl. No.: 18/042,502

(22) PCT Filed: Aug. 26, 2021

(86) PCT No.: PCT/TR2021/050860
§ 371 (c)(1),
(2) Date: Feb. 22, 2023

(87) PCT Pub. No.: WO2022/046014
PCT Pub. Date: Mar. 3, 2022

(65) Prior Publication Data

US 2023/0321373 A1 Oct. 12, 2023

(30) Foreign Application Priority Data

Aug. 26, 2020 (TR) ................................ 2020/13497

(51) Int. Cl.
*A61M 15/08* (2006.01)
*A61M 11/00* (2006.01)
*A61M 15/00* (2006.01)

(52) U.S. Cl.
CPC .......... *A61M 15/08* (2013.01); *A61M 11/001* (2014.02); *A61M 11/005* (2013.01);
(Continued)

(58) Field of Classification Search
CPC .. A61M 15/00; A61M 15/0021; A61M 15/08; A61M 11/00; A61M 11/001; A61M 11/005; A61M 11/006; A61M 16/06
See application file for complete search history.

(56) References Cited

U.S. PATENT DOCUMENTS

2009/0301472 A1* 12/2009 Kim ................. A61M 15/0085
128/200.23
2016/0279352 A1 9/2016 Wang
2016/0339188 A1 11/2016 Flickinger

FOREIGN PATENT DOCUMENTS

CN 203469157 U 3/2014
CN 104027903 A 9/2014
(Continued)

OTHER PUBLICATIONS

International Search Report and Written Opinion for International Application No. PCT/TR2021/050860, dated Dec. 17, 2021.

*Primary Examiner* — Joseph D. Boecker
*Assistant Examiner* — Jaeick Jang
(74) *Attorney, Agent, or Firm* — RAPHAEL BELLUM PLLC

(57) ABSTRACT

The present invention relates to a closed system intranasal treatment device that is preferably in round, square, rectangular, triangular prism, quadrilateral, pentagon etc. form and that ensures the person who will use it gets maximum efficiency from the drug by creating a closed structure by completely wrapping noses of pediatric, adult and geriatric patient groups and preventing the drug from passing out of the system and maximizes patient compliance, in which all liquid pharmaceutical compositions in the state of the art are applicable.

11 Claims, 4 Drawing Sheets

(52) U.S. Cl.
CPC . *A61M 15/0085* (2013.01); *A61M 2205/0294* (2013.01); *A61M 2205/3584* (2013.01); *A61M 2205/50* (2013.01); *A61M 2205/8206* (2013.01)

(56) References Cited

FOREIGN PATENT DOCUMENTS

| | | | |
|---|---|---|---|
| CN | 208893387 | U | 5/2019 |
| WO | 2019/079461 | A1 | 4/2019 |

* cited by examiner

INTRANASAL TREATMENT DEVICE

TECHNICAL FIELD OF THE INVENTION

The present invention relates to a closed system intranasal treatment device that is preferably in round, square, rectangular, triangular prism, quadrilateral, pentagon etc. form and that ensures the person who will use it gets maximum efficiency from the drug by creating a closed structure by completely wrapping noses of pediatric, adult and geriatric patient groups and preventing the drug from passing out of the system and maximizes patient compliance, in which all liquid pharmaceutical compositions in the state of the art are applicable.

STATE OF THE ART

The nose, which is an organ for smelling, is also an organ that prevents foreign substances from entering the respiratory system and is morphologically suitable for drug absorption. There are four situations in which the nasal cavity is used in drug release, these are; local therapy, systemic therapy, vaccine release and targeting to the central nervous system. The nasal route has been used for many years to provide local effect. A few of the advantages of the nasal route are as follows:

- The nasal cavity is morphologically conducive to drug absorption because the lower part of the mucous layer is rich in terms of vessels.
- It has a wide absorption area due to the large number of microvilli.
- The drug passes directly into the systemic circulation via the nasal venous route, thus the drug recovers from the first pass effect in the liver.
- Absorption rate and plasma concentration are at a level comparable to intravenous administration.
- It has a mucosal structure with low enzymatic activity.
- Its permeability is higher than other mucosal structures.
- Rapid absorption allows drugs to be administered at low doses due to high bioavailability.
- It has a fast therapeutic effect.
- It allows the administration of drugs that are metabolized from the gastrointestinal tract.
- The risk of overdose is lower.
- Large molecules can pass into the systemic circulation through the nasal mucosa.
- The human nose is a highly compatible channel that is effective in terms of drug applicability and easy in terms of patient compliance.

When state of the art is examined, anti-allergic drugs and decongestants constitute the pharmacological group that is frequently administered through nasal route. In recent years, it is set forth that the nasal drugs targeted for local effect exhibit systemic side effects, the nasal route can also be used to provide systemic effects. The number of systemic active drugs administered through nasal route is increasing in the world pharmaceutical market. In addition, vaccine companies pay attention to nasal vaccines, especially in respiratory tract infections, because the nasal mucosal immune response was quite high in the studies. The first nasal influenza vaccine was marketed in Europe in 2011 as an antigen-adjuvant system by a famous company. The second influenza vaccine gets into the market in 2003. Intranasal Live Influenza Vaccine (LAIV, FluMist™ Quadrivalent) approved for use to prevent influenza A and B virus infections, in addition to the intramuscularly administered influenza vaccines, a four-component vaccine prepared intranasally as a live, attenuated single use 0.2 ml intranasal spray has also been approved for use. However, due to the lower efficacy of protection against the H1N1 A/Bolivian subtype after the 2015-2016 pandemic, this vaccine that has been circulating in the USA, was not recommended during 2016-2017 and 2017-2018 flu seasons.

Nasal drug administration is one of the important routes of drug targeting to the brain, and it was first introduced by Dr. William II Frey in 1989. After this beginning, many studies have been carried out on intranasal drug targeting to the brain. Born et al. were able to target peptides such as melanocortin, vasopressin, and insulin to the cerebrospinal fluid within 30 minutes across the blood-brain barrier in 33 healthy subjects (9 women and 27 men) [1].

Nasal pharmaceutical dosage forms; nasal drops, hydrogels, powders, emulsions, ointments or specialized systems such as micro- and nanoparticles etc. Nasal drops are the classic dosage form of the nasal route that has been used for many years. This dosage form gives positive results for local disinfection applications; however it cannot guarantee sufficient absorption to achieve the desired systemic effect. Drugs administered in this form can be easily removed by mucociliary clearance. Hydrogels have been studied from viscous fluids to prevent mucociliary movement. In gel dosage forms, there is no risk of nasal discharge and the drug adheres to the nasal cavity. Gels are very practical and effective, especially in local treatment, and their irritation potential is low. In insulin nasal applications made with systems containing bio-adhesive hydrogel containing polyacrylic acid, bio-adhesive character was achieved to the desired extent. On the other hand, it has been determined that the use of these hydrogels in excessive concentrations reduces insulin release and causes the effect to appear in a longer time. In case a solution or suspension dosage form cannot be achieved, a dry powder form, which is one of the nasal pharmaceutical dosage forms, can be prepared. The powder dosage form is used for locally effective drugs in the nasal cavity and allows metered dosing. However, the dry powder form has serious disadvantages such as the risk of irritation in the nasal mucosa and creating a sandy feeling in the tissues. Furthermore, dry powder dosage forms are much more difficult to manufacture and costly for the patient. For these reasons, powders are not preferred for nasal application. Emulsion and ointment dosage forms are also suitable for the nasal route and locally effective drugs. However, the biggest disadvantages are its not being not administered by the patients, difficulty in formulation development, and also facing problems in metered dosing. Studies on nasal delivery of drugs with carrier systems such as micro and nano particles and liposomes are increasing day by day. However, the most important disadvantage of these systems is that the active substance interacts with the nasal mucosa for a longer time and nasal absorption increases. Because too much nasal absorption is not suitable for local effect. These systems are prepared using biocompatible polymers such that they perform extended and controlled release.

Nasal topical gasless sprays, nasal topical drops, nasal topical sticks and roll-ons, nasal systemic metered dose liquids are devices that provide nasal administration. The patient compliance of these devices is not good, especially in infants, children and elderly patients. Otherwise, these devices cannot resist mucociliary clearance because they are filled with liquid dosage form; therefore their effectiveness is low since their endurance in the nose is short.

Nasal drug administration poses a major problem in newborns, infants and children in the state of the art. Device inlet into the nose is a challenging application, especially for newborns, infants and pediatric patients. Spraying pressurized liquid in the nose reduces the patient's compliance and interrupts the treatment. Furthermore, it has physical side effects such as irritation and burning in the nasal mucosa. They are afraid of the gushing liquid medicine applications, they get hurt. In order to do this, parents have to exert a force on their children to keep the same stable and in some conditions, the application turns into an exercise of power that the child cannot interpret. The use of force is a difficult process for both parties psychologically. It prevents the drug administration from taking place at the optimum level. Thus, families can often cancel the application. Intranasal administration for parents and children is nearly as difficult as injection administration in terms of psychological process.

Children at early ages preferably breathe through the nose; they do not prefer mouth breathing. Neonates and young infants have long omega-shaped epiglottis horizontally positioned high in the pharynx very near to the soft palate than in older children and adults. Combined with the absence of paranasal sinuses, this causes less resistance to airflow in the nasal passages than in the oral route. Thus, neonates and infants prefer to breathe nasally rather than orally [2]. In case of nasal congestion, current treatments fail in practice due to the negative aspects mentioned above. If the treatment is not completed, serious sleep problems and related complications seen in the child. Therefore, existing pharmaceutical technology has the obligation to develop drug delivery methods to children that are gentle and increase their patient compliance, and devices where these applications can be performed. Intranasal devices on the market do not have good patient compliance, especially for infants and children. For this reason, effective treatment cannot be provided.

A nasal spray pump is disclosed in patent application numbered US 2012/0193377 A1. In this system, there is a reservoir extending between the closed end and the open end. Here, a single dose of the therapeutic agent is not only focused on the nose, but it is also aimed to reach regions such as hair, eyes and skin easily and effectively. In the international patent application numbered WO 2012/119153 A2; metered dose systems containing a propellant and pressurized gas that can reach the olfactory area for intranasal drug targeting to the brain derived from a drug formulation have been developed. Drug formulation is in an intranasal dosage form in powder, suspension, dispersion or liquid form. The push-in intranasal dosage form is accumulated within the olfactory region of the nasal cavity. The drug accumulated in the olfaction region is delivered to the brain by avoiding the blood-brain barrier. The hydrofluoroalkane propellant is directed into a diffuser where the intranasal dosage form is aerosolized and into the chamber containing the drug from a pressurized canister. The aerosolized intranasal dosage form passes through a nozzle and is thus delivered as a smoke to the olfactory region of the user's nasal cavity.

In the prior art patent numbered U.S. Pat. No. 9,078,814 B2, the active substance to be used with an intranasal nasal spray device containing a pharmaceutical composition is disclosed. In the patent application numbered US 2010/0122697 A1; there is negative pressure in the first foot of a U-shaped tube system, and the aerosol system in the second foot. In the system placed in two nostrils, when negative pressure is applied to one nostril, aerosol is released from the other nostril to the nasal cavity. The present invention can be used in a wide variety of ways to deliver aerosols containing drugs, preferred in many areas including known aerosol delivery systems, anesthetic vaccines, metabolites, insulin, and fragrance; it provides a method and system for nasal delivery of aerosols.

Patent application numbered WO 2007/113551 A1 relates to a nasal spray device containing a reservoir for a drug; said reservoir has a vertical plane and a neck portion disposed at an angle with respect to a base portion. It is an invention that optimizes the angle of the mouthpiece placed in the nostril of nasal sprays. The spray pump dispenser located here is attached to the neck with a push fit. Another patent application numbered US 2016/0082204 A1 in the state of the art relates to a nasal spray device for delivering a pharmaceutical formulation into the nasal cavity in metered doses.

Vibrating mesh technology (VMT) nebulizer produces aerosols (liquid solution converted to micron-level droplets) using a piezoelectric ceramic and mesh, it is portable, relatively quiet and, unlike ultrasonic nebulizers, did not require heating nebulization solutions [3]. A vibrating mesh technology nebulizer consists of a liquid tank with a piezo mesh disk mounted on one side and a microprocessor unit with a driver circuit board with batteries. This piezoelectric material has a network of thousands of precision formed holes by laser and is in contact with the liquid solution. It vibrates at high frequencies when driven by an analog signal at a certain frequency and voltage. As a result of the rapid vibration, the solution is drawn through the holes to form droplets of consistent size (aerosol), which are delivered at a low rate for direct inhalation.

The driving frequency of the piezoelectric material should be equal to the resonance frequency of the material. In this way, the nebulizer operates in its most efficient state. In addition, other factors affecting the efficient operation of the nebulizer are nebulization properties such as solution outlet rate, mesh size and particle size, and physicochemical properties of solutions [4,5].

Recent researches show that there is a relationship between outlet speed and voltage at a fixed resonant frequency, and outlet speed increases with driving voltage [6]. Piezoelectric material vibrates most at its own resonant frequency and drug solution discharge rates reach to its peak when the driving frequency is close to the resonance frequency of the piezoelectric ceramic [7,8]. However, the actual resonant frequencies are different from the nominal resonant frequencies given by the manufacturers. The resonant frequency depends on the impedance changes induced by the temperature and pressure of the piezoelectric material and/or the viscosity of the medium [9]. It has been found in the researches that even a 1% incompliance between the actual resonant frequency of the device and the signal frequency generated by the driver circuit leads to inefficient device usage. This 1% incompliance causes the drug to worsen the droplet exit rate from the device by 11-30%, increase the droplet size by 1.6-7.7%, and draw 6.6-13.6% more current from the battery [10].

It is necessary to provide a nasal device due to the limitations and inadequacies of the solutions in the state of the art which ensures that the person who will use it gets maximum efficiency from the drug by creating a closed structure by completely wrapping their noses and preventing the drug from passing out of the system and maximizes patient compliance, in which all liquid pharmaceutical compositions in the state of the art are applicable, performs nasal application without inserting a device into the nose.

BRIEF DESCRIPTION AND OBJECTS OF THE INVENTION

In the present invention, a closed system intranasal treatment device that is preferably in round, square, rectangular, triangular prism, quadrilateral, pentagon etc. form and that ensures the person who will use it gets maximum efficiency from the drug by creating a closed structure by completely wrapping the nose and preventing the drug from passing out of the system and maximizes patient compliance, in which all liquid pharmaceutical compositions in the state of the art are applicable, is disclosed.

An object of the invention is to provide effective and practical application of drugs to the nose in children. In addition to the optimum effective application of the drug with the device of the present invention, it is easier to apply compared to the devices of the state of the art.

Another object of the invention is to maximize patient compliance by preventing drug leakage to the outside. The leakage of the drug to the outside is prevented by means of the closed shape of the device of the present invention, which provides ease of use and fits perfectly on the nose and patient compliance is increased to much higher levels without applying pressure as in spray dosage forms. The greater the efficiency of drug administration, the lower dose of drug administered, accordingly, the duration of application and side effects decrease and patient compliance increases. Patient compliance is increased to much higher levels without applying pressure as in spray dosage forms with the invention.

Another object of the invention is to provide a device in which formulations in solution form can be administered. The formulations can be prepared in solution form more easily than the devices in the state of the art in the device of the present invention. Furthermore, the absorption of the solution form in the application area and therefore its effectiveness is faster and more effective than other (semi-solid, solid, etc.) dosage forms.

The device according to present invention allows effective intranasal drug administration in both pediatric and normal adults for many active substances available in the market. The device according to present invention allows more effective application with effects such that the application does not require hand-arm coordination compared to other intranasal delivery devices, the person is able to take the drug with the normal breathing pattern without the need to take a special position after it is inserted into the nose, it stays in the application area more efficiently than other intranasal administration routes due to its closed system.

Another object of the invention is to increase the effectiveness of the drug by extending its remaining time in the nose. When the device of the present invention is used with both liquid and in-situ systems (formulations that are liquid at room temperature and are gelated at nasal pH and body temperature when targeted to the nose), the effectiveness of the drug is further increased by extending its remaining time in the nose. The device of the present invention is compatible with liquid dosage forms. In-situ systems are also in liquid form within the device and are systems that provide gelation after application to the body. For this reason, in-situ systems are compatible with the intranasal delivery device, since the production and filling stages are in liquid dosage form. Since these in-situ systems are gelated in the nose unlike liquid dosage forms after the application, it is ensured that the active substance remains in the nose for a longer time.

Another object of the invention is to distribute the drug homogeneously in the nose when nasal application is made. The drops coming out of the spray are effective in a certain area with a certain angle in conventional nasal delivery devices (nasal sprays, etc.), and it is not possible for the drug to reach the entire nasal cavity. The problem of the drugs not being distributed homogeneously all over the nose which is the biggest disadvantage of conventional nasal sprays and drops, is eliminated, and homogeneous distribution of the drug in the nose is ensured with the present invention. The mechanism in the intranasal delivery device which will ensure spraying targets the drug in the form of mist to the nasal mucosa and ensures that the drug reaches the entire nasal cavity homogeneously.

Another object of the invention is to provide a painless nasal application without the need for an extra apparatus. Nasal application can be performed without requiring any action against the integrity of the body, such as inserting or pushing any apparatus (dropper, pipette, silicone cap, etc.) into the nostrils with the invention, the patient inhales the medicine to be applied in the form of soft mist painlessly and indolently and the process is carried out without even being aware that the medicine is being applied with the closed system. Also, since it does not apply pressure and pressure to the noses of children as in the devices on the market, the use of force by parents is eliminated by means of the soft mist technology assisted aerosol application of the invention.

Another object of the invention is to provide maximum benefit to the person with the drug applied by minimizing the leakage of the drug to the outside of the nose, by means of its closed system.

Another object of the invention is to provide a device with high patient compliance, especially in pediatric patients. The drug reservoir, which is embedded in the portion of the device that is attached to the patient's nose, is remotely controlled by a piezoelectric crystal mechanism that will be triggered by remote electromagnetic waves in the invention. Therefore, no connection cable, tube or injector is required other than the skeletal system attached to the nose, and the design is free from attachments. Thus, patient compliance is ensured to be even higher, since pediatric patients will not feel that they are exposed to a mechanism.

Another object of the invention is to provide a nasal delivery device that can be dosed with medication. In particular, the weight values of infants up to the age of 2 change every week. Dosing can be made based on the personal information of the patient, which can be controlled remotely in the device of the present invention. The drug dose to be given to the patient can be adjusted in the device according to the personal information of the patients (weight, height, age, gender, etc.), by means of the communication of the Bluetooth unit, microprocessor unit and driver circuit in the nebulizer in the aforementioned device with smart mobile devices (smartphone, etc.) and triggering the piezoelectric crystal material in the device skeletal system.

Another object of the invention is to ensure that the skin is not irritated and to provide comfortable breathing during nasal application with the device. It provides easy breathing through the nose due to the fact that the carrier part of the device of the present invention which is attached to the nose is a sponge or a soft and breathable material like a sponge. Also, the device does not damage the outer surface of the nose and does not irritate the skin with the soft texture of the device.

Another object of the invention is to ensure that the optimum drug remains in the nose in a nasal application. It is ensured that the optimum drug remains in the nose by creating a second obstacle for the aerosol vapor to escape from the device, by means of the ladybug wings, which are in the form of a shutter system that open during drug application to the upper part of the skeletal system and close the outer walls of the skeleton.

Another object of the invention is to provide a product that can be used easily by both adults and children in all patient groups and in all liquid dosage forms for nasal administration on the market.

Another object of the invention is to prevent unnecessary formulation release during breathing in nasal applications. Unnecessary formulation release is prevented during breathing in the device of the present invention with the special port that opens only during breathing in the drug reservoir containing the aerosol cloud.

In addition to the local treatment of nose and lungs diseases with the device developed within the scope of the invention, active substances that will provide systemic effects can also be applied from these application areas. In addition, drug targeting to the brain can be performed with this device via intranasal route.

Drug doses can be adjusted according to age, height and weight for the patients with the invention. In addition, drug release can be provided and controlled with the remote control device.

DEFINITIONS OF ELEMENTS/SECTIONS/PARTS THAT CONSTITUTE THE INVENTION

Figure 1:
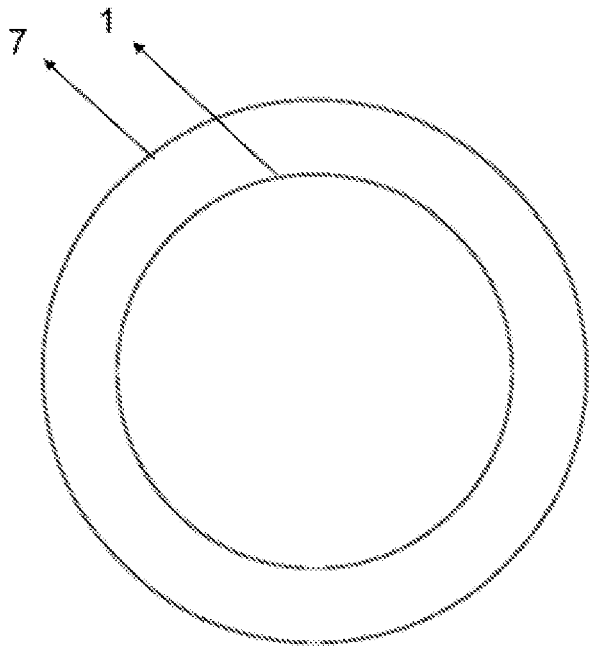
FIG. 1: Top view of the invention.
Figure 2:
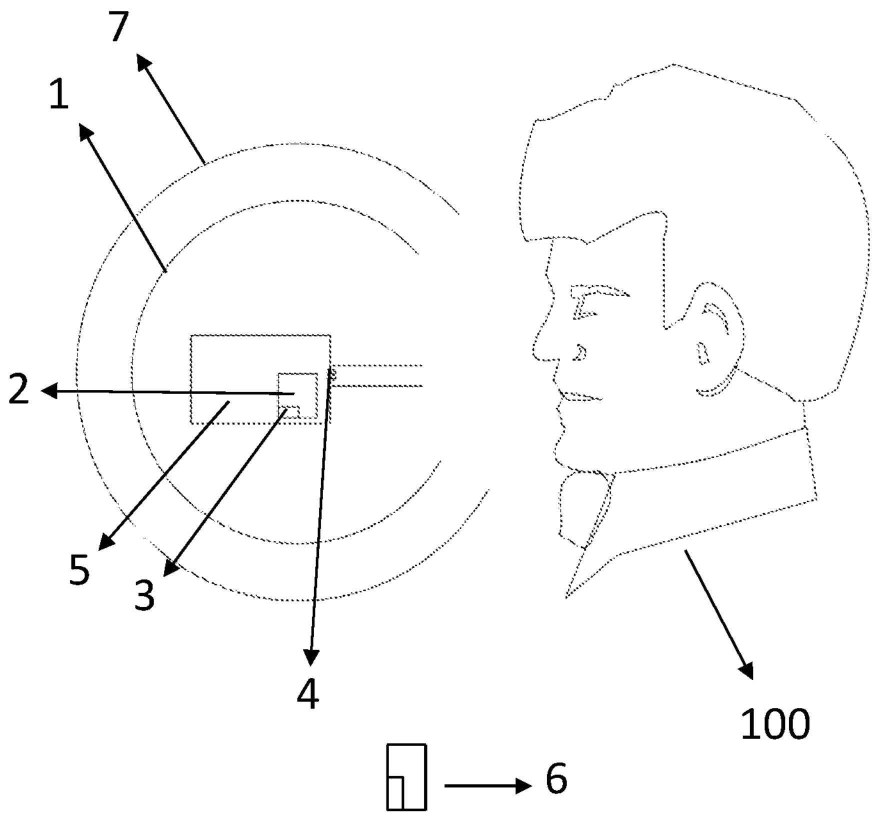
FIG. 2: Side view of the interior of the invention.

The parts and sections in the figures are enumerated and the corresponding of each number is given below in order to better explain this invention:

1—Skeletal System
2—Drug Reservoir
3—Battery
4—Holes
5—Nebulizer
6—Remote Control
7—Ladybug Wings
100—User

DETAILED DESCRIPTION OF THE INVENTION

The present invention relates to an intranasal treatment device which ensures that the person who will use it gets maximum efficiency from the drug by creating a closed structure by completely wrapping their noses and preventing the drug from passing out of the system and maximizes patient compliance, in which all liquid pharmaceutical compositions in the state of the art are applicable.

It comprises skeletal system (1) that can be designed in different geometric shapes (round, square, rectangle, triangle, prism, square, pentagon, etc.) preferably round to completely cover the nose, drug reservoir (2) (reservoir), which can be produced in the form of a tube or in different geometric shapes within this system and filled with drugs in liquid form, holes (4) that allow the incoming liquid drug to become aerosol droplets with the desired particle spacing (2-15 micrometers) in the targeting region, nebulizer (5), which enables the dosage form in the medication chamber (reservoir) (2) to become aerosol droplets as it passes through the holes (4), remote control (6), which allows the device to be controlled remotely, battery (3), which provides the power needed by the nebulizer (5) while operating with electrical energy, software that enables the nebulizer (5) to be operated with or without a battery (3) with a mobile phone or different signal sending devices, and to adjust the patient doses according to age, height and weight, ladybug wings (7) which has a structure in the form of a shutter system that opens to the upper part of the skeletal system (1) during drug application and that will close the outer wall of the skeletal system (1) and at the same time prevents aerosol droplets released from the holes (4) in the skeletal system (1) from escaping out of the device skeletal system (1). In one embodiment of the invention, the device further comprises an activation button that can target the drug into the nose, providing a slow and gentle drug release when activated/pressed. In an embodiment of the invention, the nasal treatment device also has the opportunity to operate with a battery other than a cell battery or to operate by being charged remotely/wirelessly.

In another embodiment of the invention, said intranasal treatment device;

- skeletal system (1), which has a structure to completely cover the nose and preferably has a round shape and surrounds the mechanism from the outside,
- drug reservoir (2), which can be produced in the form of a tube or in different geometric shapes inside the mechanism and filled with drugs in liquid form,
- a piezoelectric crystal material located next to the drug reservoir (2) inside the skeletal system (1),
- battery (3), which provides the power that the nebulizer (5) needs while working,
- holes (4) that enable the incoming drug in liquid form to transform into aerosol droplets with the desired particle ratio in the targeting region,
- nebulizer (5) which allows the dosage form to become aerosol droplets as it passes through the holes (4) contained in the drug reservoir (2), operates the intranasal treatment device with a smart mobile device and adjusts patient doses according to age, height, weight and/or gender,
- ladybug wings (7) which opens during drug administration to the upper part of the skeletal system (1) and has a structure in the form of a shutter system to close the outer wall of the skeletal system (1) and at the same time prevents aerosol droplets released from the holes (4) from escaping out of the device skeletal system (1)

In this embodiment, said device may also comprise a remote control (6) or a mobile device containing Bluetooth that allows the device to be controlled remotely. Also in this embodiment, said device may further include an activation button.

The operating principle of the nasal treatment device is in two-stages. First, the drug in liquid form is directed by an electronic system to the micro-sized holes (4) that will form the aerosol form, in this way, the formation of soft mist or precise spray content that can move slowly is ensured. The aerosol droplets released from the device are ensured to reach the nasal cavity without loss by means of the skeleton system (1) in the second stage. The present invention is placed in the nose of the user and when it is ready, it provides a soft mist aerosol cloud release during the application period of 5 minutes on average although it varies according to the type of drug and for what purpose the patient uses it. Nasal drug administration is based on an electromechanical aerosol generation system such as the vibrating screen method.

The drug reservoir (2) comprises a soft mist aerosol containing medicine in liquid form for nasal administration; it has a compact structure with the entire device. The skeletal system (1) is preferably spongy, preferably ball-shaped, with the feature of covering the nose in a compact structure. The drug in liquid form, which is kept in the drug reservoir (2), will target the drug into the nose by providing a slow and gentle release when the device skeletal system (1) is inserted into the nose and the activation button is pressed. The drug reservoir (2), which is embedded in the skeletal system (1) attached to the nose, can be controlled by a remote control (6) by means of a piezoelectric crystal material to be triggered by remote electromagnetic waves. Said piezoelectric crystal material is located in the skeletal system (1) next to the drug reservoir (2). Age-weight-dose calculation and follow-up will be possible with a software program to be installed on the smart phone or the control panel designed for this device by means of the dosing controllable with the remote control (6). Nebulizer (5) comprises Bluetooth unit, microprocessor unit, driver circuit.

Figure 3:
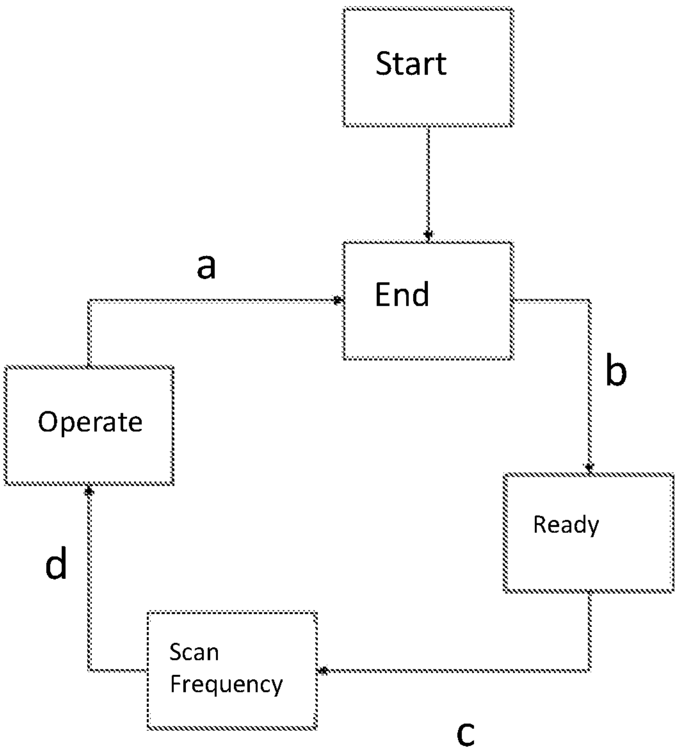
FIG. 3: The exemplary operating principle of the device according to the present invention is as follows; a) aerosol exhausted, low battery, trigger signal received, b) trigger signal received (Bluetooth, button pressed), c) full battery, d) resonance frequency found.

After the resonance frequency of the piezoelectric crystal material used in the intranasal therapy device of the invention is found, the device should be operated. For this reason, the driver circuit in the device is first used to find this resonant frequency. In FIG. 3, the exemplary operating principle of the device according to the present invention is given. The first operation of the device is enabled either by means of pressing the activation button on the device mechanically or by sending a trigger signal wirelessly from a smartphone application via Bluetooth. Then the battery status is checked and if appropriate, the microprocessor unit and the driver circuit start the frequency scanning process and finds the actual resonant frequency of the piezoelectric material. After the frequency is found, the driver circuit drives the piezoelectric material with an analog signal at the specified voltage and frequency and the piezoelectric material vibrates. If the liquid form in the medicine tank is finished, or if a stop trigger signal is received with a low battery, the driver circuit stops driving the signal and operation is terminated.

Figure 4:
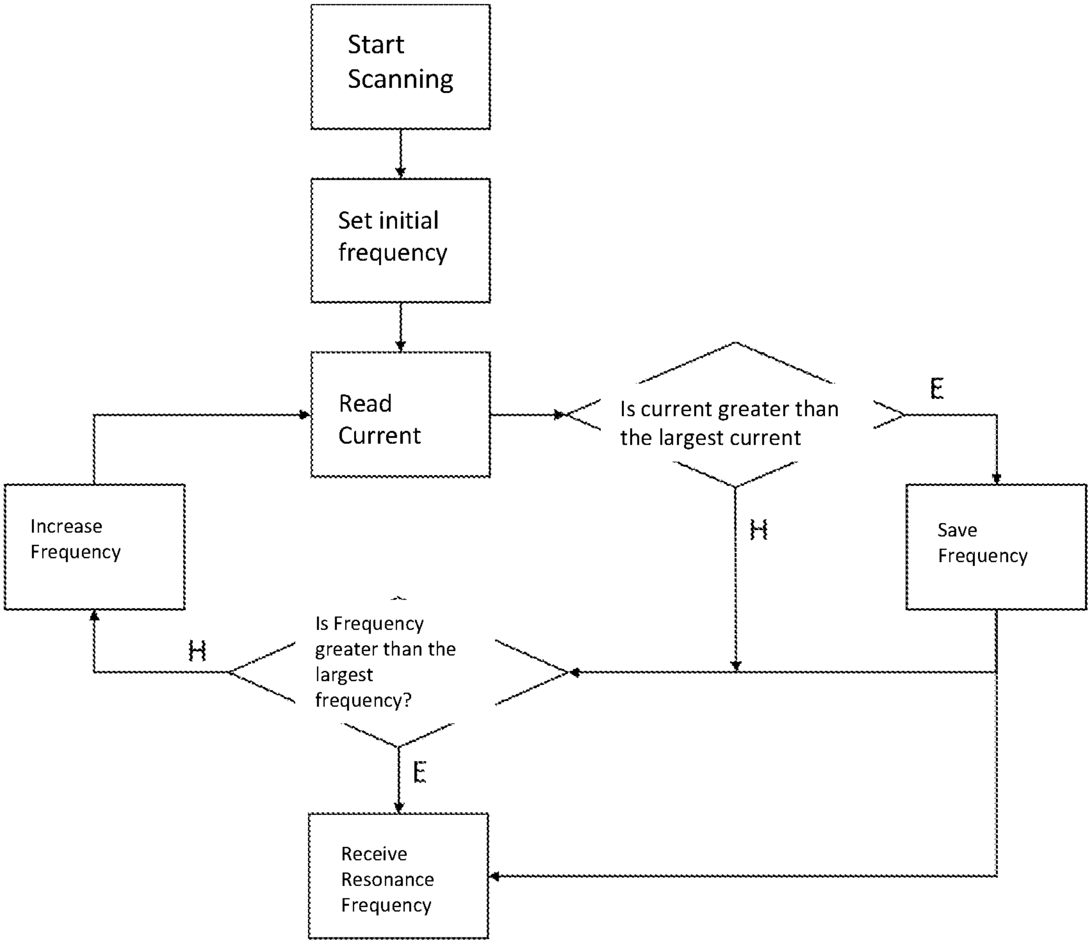
FIG. 4: The resonant frequency scanning algorithm to run on the microprocessor in the device of the present invention.

In FIG. 4, the resonant frequency scanning algorithm to run on the microprocessor is given. This algorithm finds the true resonance frequency of the piezoelectric crystal material by scanning between the start and end frequencies. The start and end frequencies can be selected as 10% below and above the nominal resonance frequency of the material. After the initial frequency is set and the analog signal is applied to the material with the driver circuit, the current is read. The current is read each time and the frequency of the signal with the greatest current is recorded by continuing to generate the signal in the determined frequency range. At the end of scanning, the frequency of the signal that draws the greatest current from the battery is the true resonance frequency of the piezoelectric crystal material.

Figure 5:
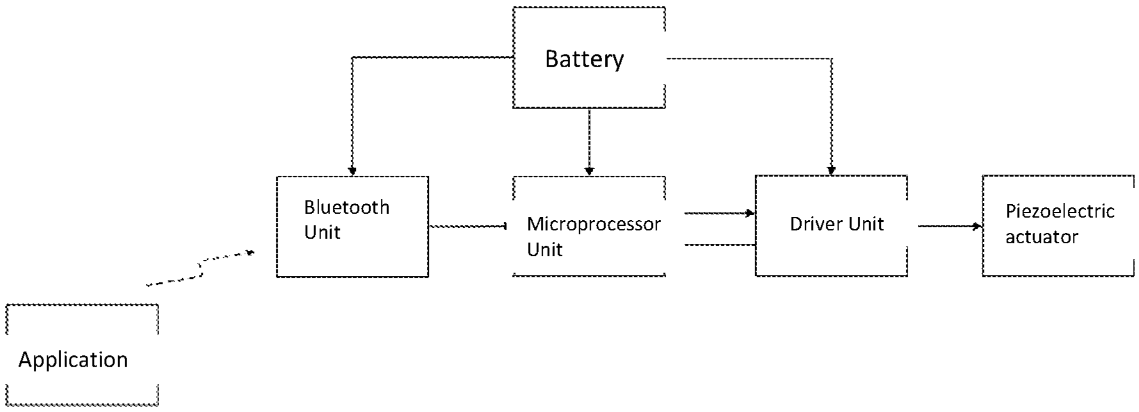
FIG. 5: Circuit block diagram for the vibration of the piezoelectric crystal material in the intranasal treatment device of the present invention.

In FIG. 5, circuit block diagram for the vibration of the piezoelectric crystal material in the intranasal treatment device of the present invention is given.

The operating method of the intranasal therapy device of the present invention is as follows;

Ensuring communication between the smartphone and the device via the Bluetooth unit and taking the patient's height, weight, age and/or gender information required to adjust the drug dose for the patient, and transmitting the trigger signal generated for this to the microprocessor unit, Processing of the trigger signal coming to the microprocessor unit by the microprocessor unit and determining of the resonance frequency of the piezoelectric crystal material, Generating a signal at the resonant frequency determined by the microprocessor unit and transferring it to the piezoelectric crystal material by means of the driver circuit, Vibration of piezoelectric crystal material, Spraying the drug, which is transformed into aerosol droplets in particle size determined according to the drug dose adjusted for the patient according to the personal data, through the holes (4) By triggering the medicine chamber (2) of the vibrating piezoelectric crystal material.

In normal operating mode, the device now continues to communicate with the smart mobile device (e.g. smart phone). The smartphone application is used both before the device starts to operate and while it is running. Before the device starts to work, settings such as user selection, dose selection, time selection can also be made via the smart mobile device. Also, selecting patient's height, weight, age and/or gender information via the smart mobile device can be performed and the dose to be given to the patient is determined according to this information. Furthermore, in an embodiment of the invention, the information read from the sensors in the device such as the date and time when the user uses the intranasal therapy device, the pressure, temperature, humidity and orientation in the device while it is being used are sent to the smart mobile device via the Bluetooth unit in the device and recorded via the application here.

The operating system of the device, which is a closed system to cover the entire nose, starts with the release of the drug from the drug reservoir (2) placed inside the skeletal system (1). Here, the dosage of the drug is adjusted according to factors such as the patient's age, gender, height-weight ratio, and pumped at the required level via the developed software. Then, the 128,000 holes of the nebulizer, which uses electrical energy and vibrating screen technology (VMT), begin to vibrate, the dosage form (solution, emulsion or suspension) in the drug reservoir turns into aerosol droplets while it passes through this vibrating screen system.

When it is desired to target drugs to the nose and brain, the particle size of aerosol droplets should be 10-15 micrometers. When it is desired to target local drugs to the lungs, the particle size of aerosol droplets should be 2-6 micrometers. When it is desired to target systemic drugs to the lungs, aerosol droplets should have a particle size below 1 micrometer. The size difference here is realized by the holes (4) and the vibration frequency of the holes in the skeletal system (1) of the device.

The skeletal system (1) attached to the nose of the device consists of a spongy material. However, as an alternative to this, the material of the skeletal system (1) can be made of plastic, sponge rubber, polymer-derived materials that are compatible with the body and do not cause any harm. The ladybug wings (7), which have a structure in the form of a thin shutter system to be opened on the skeletal system (1), which is produced in a spongy structure, creates a second obstacle for the aerosol vapor to escape from the device and ensures that the optimum drug remains in the nose during the application of drug.

In another embodiment of the invention, it is possible to use the device without electrical energy. In such usages, the electric nebulizer (5), the battery (3) providing energy to the nebulizer (5) and the software designed in accordance with the nebulizer (5) are removed from the system; there is an air balloon in the skeletal system (1) of the device and at least one syringe in contact with this air balloon. The air within the syringe applies mechanical force to the air balloon and ensures the air balloon to inflate and the formation of pressure therein. When the syringe is filled with air, an average pressure of 10 bar occurs. There are air balloons that ensure the delivery of the drug solution inside the drug reservoir to the hole system (4) with this pressure, and ladybug wings (7) that prevent the escape of aerosol droplets to the outside. In such uses, the electronic system becomes mechanical since the nebulizer (5) is removed from the system.

In another embodiment of the invention, there is a spring system placed inside the skeletal system (1) and a latch in connection with this spring system in the device. This latch is placed outside the skeletal system (1) of the device, the spring system starts to stretch when the latch is started to be turned by hand and this energy is provided to push the dosage form in the drug reservoir (2) to the nasal spray jet. The nasal spray jet contained here is the system in which the liquid used in nasal washing solutions in traditional nasal drops is sprayed into the nose. This system provides placement within the closed skeletal system (1) at an angle that targets both nostrils at an angle corresponding to the nostrils. Pressure is provided by a mechanical system, not an electronic system, next to the drug reservoir (2), the holes (4) and the ladybug wings (7) in this system. This pressure is a mechanical system as mentioned in the alternative embodiment above.

In the alternative embodiments mentioned above, the drug reservoir (2), the holes (4) and the ladybug wings (7) remain the same, making it possible to use the system mechanically instead of electronically in cases where the pressure that enables the system to operate is not electrical or the battery is dead.

The device according to the present invention requires a reservoir area of 300 μL at most for 5 minutes of application. The droplet size of the aerosols to be released or sprayed from the device is in the range of 10-15 μm for targeting to the nose and brain, 2-6 μm for local drug targeting to the lungs, and below 1 micrometer for systemic drug targeting to the lungs.

REFERENCES

1. Born J, Lange T, Kern W, McGregor G P, Bickel U, Fehm H L. 2002. Sniffing neuropeptides: A transnasal approach to the human brain. Nat Neurosci 5:514-516.
2. Saikia D, Mahanta B. Cardiovascular and respiratory physiology in children. Indian J Anaesth. 2019 September; 63(9):690-697.
3. Ari, A., 2014. Jet, ultrasonic, and mesh nebulizers: an evaluation of nebulizers for better clinical outcomes.
4. Ghazanfari, T., Elhissi, A. M., Ding, Z. and Taylor, K. M., 2007. The influence of fluid physicochemical properties on vibrating-mesh nebulization. International journal of pharmaceutics, 339(1-2), pp. 103-111.
5. Hertel, S., 2014. Pulmonary delivery of pharmaceutical proteins by means of vibrating mesh nebulization (Doctoral dissertation, Imu).
6. Yan, Q., Wu, C. and Zhang, J., 2019. Effect of the dynamic cone angle on the atomization performance of a piezoceramic vibrating mesh atomizer. Applied Sciences, 9(9), p. 1836.
7. Kuo, Y. M., Chan, W. H., Lin, C. W., Huang, S. H. and Chen, C. C., 2019. Characterization of vibrating mesh aerosol generators. Aerosol and Air Quality Research, 19(8), pp. 1678-1687.
8. Yan, Q., Sun, W. and Zhang, J., 2020. Study on the Influencing Factors of the Atomization Rate in a Piezoceramic Vibrating Mesh Atomizer. Applied Sciences, 10(7), p. 2422.
9. Huynh, T. C. and Kim, J. T., 2017. Quantification of temperature effect on impedance monitoring via PZT interface for prestressed tendon anchorage. Smart Materials and Structures, 26(12), p. 125004.
10. Moon, S. H., Chang, K. H., Park, H. M., Park, B. J., Yoo, S. K. and Nam, K. C., 2021. Effects of Driving Frequency and Voltage on the Performances of Vibrating Mesh Nebulizers. Applied Sciences, 11(3), p. 1296.

The invention claimed is:

1. A closed system nasal treatment device for children and adults, that ensures a patient who will use it gets maximum efficiency from a drug by creating a closed structure by completely wrapping the nose of the patient and preventing the drug from passing out of the nasal treatment device and maximizes patient compliance, in which applicable to liquid pharmaceutical compositions, the nasal treatment device comprises:

a skeletal system (1), which has a structure configured to completely cover the nose of the patient;

a drug reservoir (2), which can be produced in the form of a tube or in different geometric shapes inside the nasal treatment device and filled with drugs in liquid form and which provides a soft mist aerosol;

a battery (3) or a cell battery that can be charged remotely via wired or wireless, which provides a power that a nebulizer (5) needs while working;

holes (4) that enable the incoming drug in liquid form to transform into the soft mist aerosol droplets with a desired particle ratio in a targeting region;

the nebulizer (5) which allows the liquid form in the drug reservoir (2) to become the soft mist aerosol droplets as it passes through the holes (4);

a mobile phone configured to be a remote control (6) that allows the device to be controlled remotely;

software to be installed on the mobile phone that enables the nebulizer (5) to be operated with or without the battery (3), and to adjust the dose according to the age, height, and weight of the patient; and ladybug wings (7) having a structure in the form of a shutter system that opens to an upper part of the skeletal system (1) during drug administration configured to close an outer wall of the skeletal system (1) and prevents the soft mist aerosol droplets released from the holes (4) from escaping out of the skeletal system (1).

2. The nasal treatment device of claim 1, wherein a shape of the skeletal system (1) is a round ball, a square, a rectangular, a triangular prism, a quadrilateral, or a pentagon.

3. The nasal treatment device of claim 2, wherein the shape of the skeletal system (1) is the round ball.

4. The nasal treatment device of claim 1, wherein the nasal treatment device is configured to be charged independent from the cell battery via the battery, wired or wirelessly.

5. The nasal treatment device of claim 1, wherein the nasal treatment device further comprises an activation button configured to target the drug into the nose.

6. A method of operating the nasal treatment device of claim 5, the method comprising:

turning on the nasal treatment device by activating the activation button;

ensuring communication between the mobile phone and the nasal treatment device via a Bluetooth unit, taking the height, weight, age, and/or gender information of the patient required to adjust the drug dose for the patient, and transmitting a trigger signal generated for this to a microprocessor unit;

processing of the trigger signal coming to the microprocessor unit by the microprocessor unit and determining a resonance frequency of a piezoelectric crystal material;

generating a signal from the determined resonance frequency by the microprocessor unit and transferring the signal to the piezoelectric crystal material by a driver circuit;

vibrating the piezoelectric crystal material; and spraying the drug transformed into the soft mist aerosol droplets in a particle size according to the drug dose adjusted according to the height, weight, age, and/or gender information of the patient, through the holes (4) by triggering the drug reservoir (2) through the vibrating of the piezoelectric crystal material.

7. An intranasal treatment device which ensures that a patient who will use it gets maximum efficiency from a drug by creating a closed structure by completely wrapping the nose of the patient and preventing the drug from passing out of the intranasal treatment device and maximizes patient compliance, in which applicable to liquid pharmaceutical compositions, the intranasal treatment device comprises:

a skeletal system (1), which has a structure configured to completely cover the nose of the patient;

a drug reservoir (2), which can be produced in the form of a tube or in different geometric shapes inside the intranasal treatment device and filled with drugs in liquid form and which provides a soft mist aerosol;

a piezoelectric crystal material located next to the drug reservoir (2) inside the skeletal system (1);

a battery (3) or a cell battery that can be charged remotely via wired or wireless, which provides a power that a nebulizer (5) needs while working;

holes (4) that enable the incoming drug in liquid form to transform into the soft mist aerosol droplets with a desired particle ratio in a targeting region;

the nebulizer (5) which allows the liquid form in the drug reservoir (2) to become the soft mist aerosol droplets as it passes through the holes (4), operates the intranasal treatment device with a smart mobile device, and adjusts the dose according to the age, height, weight, and/or gender of the patient; and ladybug wings (7), having a structure in the form of a shutter system that opens to an upper part of the skeletal system (1) during drug administration configured to close an outer wall of the skeletal system (1) and prevents the soft mist aerosol droplets released from the holes (4) from escaping out of the skeletal system (1).

8. The intranasal treatment device of claim 7, wherein the nebulizer (5) comprises a Bluetooth unit, a microprocessor unit, and a driver circuit, and wherein the nebulizer (5) is configured to trigger the piezoelectric crystal material by remote electromagnetic waves to adjust the dose and drug release according to the age, height, weight, and/or gender of the patient.

9. The intranasal treatment device of claim 8, further comprising smart mobile device, wherein the smart mobile device comprises a Bluetooth unit that allows the nebulizer (5) device to be controlled remotely and enables data communication between the smart mobile device and the intranasal treatment device.

10. The intranasal treatment device of any one of claims 7-9, further comprising an activation button.

11. A method of operating the intranasal treatment device of claim 10, the method comprising:

turning on the intranasal treatment device by activating the activation button;

ensuring communication between the smart mobile device and the intranasal treatment device via the Bluetooth unit, taking the height, weight, age, and/or gender information of the patient required to adjust the drug dose, and transmitting a trigger signal generated for this to the microprocessor unit;

processing the trigger signal coming to the microprocessor unit by the microprocessor unit and determining a resonance frequency of the piezoelectric crystal material;

generating a signal from the determined resonance frequency by the microprocessor unit and transferring the signal to the piezoelectric crystal material by the driver circuit;

vibrating the piezoelectric crystal material; and spraying the drug transformed into the soft mist aerosol droplets in a particle size according to the drug dose adjusted according to the height, weight, age, and/or gender information of the patient through the holes (4) by triggering the medicine drug reservoir (2) through the vibrating the piezoelectric crystal material.

* * * * *